United States Patent
Flanagan et al.

(10) Patent No.: US 7,037,252 B2
(45) Date of Patent: May 2, 2006

(54) BRACHYTHERAPY SEED TRANSPORT DEVICES AND METHODS FOR USING SAME

(75) Inventors: Richard J. Flanagan, Saint-Lazare (CA); R. William Riddoch, Pierrefonds (CA); Pierre Morel, Kirkland (CA)

(73) Assignee: DRAXIS Specialty Pharmaceuticals, Inc., Kirkland (CA)

( * ) Notice: Subject to any disclaimer, the term of this patent is extended or adjusted under 35 U.S.C. 154(b) by 0 days.

(21) Appl. No.: 10/430,107

(22) Filed: May 5, 2003

(65) Prior Publication Data

US 2004/0225176 A1   Nov. 11, 2004

(51) Int. Cl.
*A61M 36/00* (2006.01)
*A61N 5/00* (2006.01)

(52) U.S. Cl. .......................................................... 600/7
(58) Field of Classification Search .................. 600/1–8,
600/18, 141, 144, 145, 331, 344, 345, 427,
600/433, 585; 221/211; 222/168, 363; 376/158,
376/202; 128/897, 898; 424/1.29, 1.11,
424/4.13, 422, 426; 251/124; 29/401.1;
250/506.1; 523/218, 219; 428/320.2; 534/696,
534/697, 700, 703, 710, 711, 722, 723; 514/411;
606/130; 604/57–64, 187, 523, 524–527,
604/164.01, 264–266, 890.1, 891.1, 110,
604/272
See application file for complete search history.

(56) References Cited

U.S. PATENT DOCUMENTS

| | | | | |
|---|---|---|---|---|
| 4,402,308 A | * | 9/1983 | Scott | 600/7 |
| 4,509,506 A | * | 4/1985 | Windorski et al. | 600/8 |
| 4,697,575 A | * | 10/1987 | Horowitz | 600/8 |
| 4,815,449 A | * | 3/1989 | Horowitz | 600/7 |
| 5,460,592 A | * | 10/1995 | Langton et al. | 600/7 |
| 5,561,173 A | * | 10/1996 | Dry | 523/218 |
| 5,630,409 A | | 5/1997 | Bono et al. | 128/200.18 |
| 5,713,828 A | * | 2/1998 | Coniglione | 600/7 |
| 5,906,574 A | * | 5/1999 | Kan | 600/7 |
| 5,928,130 A | * | 7/1999 | Schmidt | 600/7 |
| 6,013,020 A | * | 1/2000 | Meloul et al. | 600/7 |
| 6,102,844 A | * | 8/2000 | Ravins et al. | 600/8 |
| 6,113,529 A | * | 9/2000 | Shi | 600/7 |
| 6,159,143 A | * | 12/2000 | Lennox | 600/4 |
| 6,264,600 B1 | * | 7/2001 | Grimm | 600/7 |
| 6,402,677 B1 | * | 6/2002 | Jacobs | 600/7 |
| 6,419,866 B1 | | 7/2002 | Karl et al. | 264/148 |
| 6,450,937 B1 | * | 9/2002 | Mercereau et al. | 600/7 |
| 6,450,938 B1 | | 9/2002 | Miller | 600/7 |
| 6,497,647 B1 | * | 12/2002 | Tucker | 600/8 |

(Continued)

OTHER PUBLICATIONS

Langely, S. E. et al., "Prostate brachytherapy has come of age: a review of the technique and results," *R. BJU Int'l*, 2002, 89, 241-249.

*Primary Examiner*—Samuel G. Gilbert
(74) *Attorney, Agent, or Firm*—Woodcock Washburn LLP

(57) ABSTRACT

Devices, systems, and methods are provided for transporting implants. In one embodiment, the implants are radioactive seeds contained within substantially transparent sleeves that can be sealed at both ends. Multiple sleeves can be placed in a transfer device that, in turn, can be placed in a canister for further protection. The entire assembly can be sterilized prior to shipment to the user. Upon receipt, one can verify the loading pattern and activity of each sleeve, open one of the seals, and transfer the contents into a brachytherapy needle.

25 Claims, 5 Drawing Sheets

U.S. PATENT DOCUMENTS

| | | | |
|---|---|---|---|
| 6,514,193 B1 | 2/2003 | Kaplan | 600/7 |
| 6,530,875 B1 * | 3/2003 | Taylor et al. | 600/7 |
| 6,554,760 B1 | 4/2003 | Lamoureux et al. | 600/7 |
| 6,569,076 B1 * | 5/2003 | Larsen et al. | 600/3 |
| 6,572,525 B1 * | 6/2003 | Yoshizumi | 600/7 |
| 6,575,888 B1 * | 6/2003 | Zamora et al. | 600/3 |
| 6,582,354 B1 * | 6/2003 | Ellard | 600/8 |
| 6,639,237 B1 * | 10/2003 | Pedersen et al. | 250/506.1 |
| 6,648,811 B1 | 11/2003 | Sierocuk et al. | 600/7 |
| 6,656,106 B1 | 12/2003 | Schmidt | 600/7 |
| 6,709,381 B1 * | 3/2004 | Munro, III | 600/3 |
| 2001/0005930 A1 * | 7/2001 | Coniglione | 29/401.1 |
| 2003/0097035 A1 * | 5/2003 | Tucker et al. | 600/8 |
| 2003/0109769 A1 * | 6/2003 | Lowery et al. | 600/7 |
| 2003/0171639 A1 * | 9/2003 | Taylor et al. | 600/7 |
| 2003/0191355 A1 * | 10/2003 | Ferguson | 600/3 |

* cited by examiner

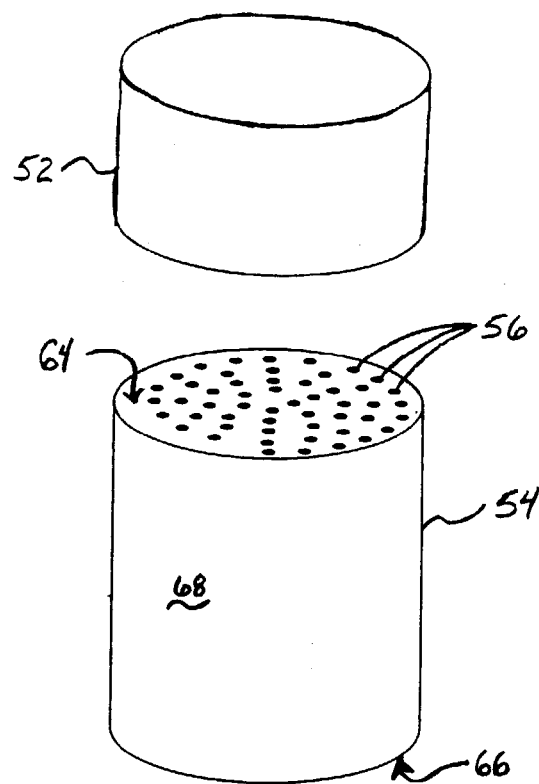
FIGURE 3
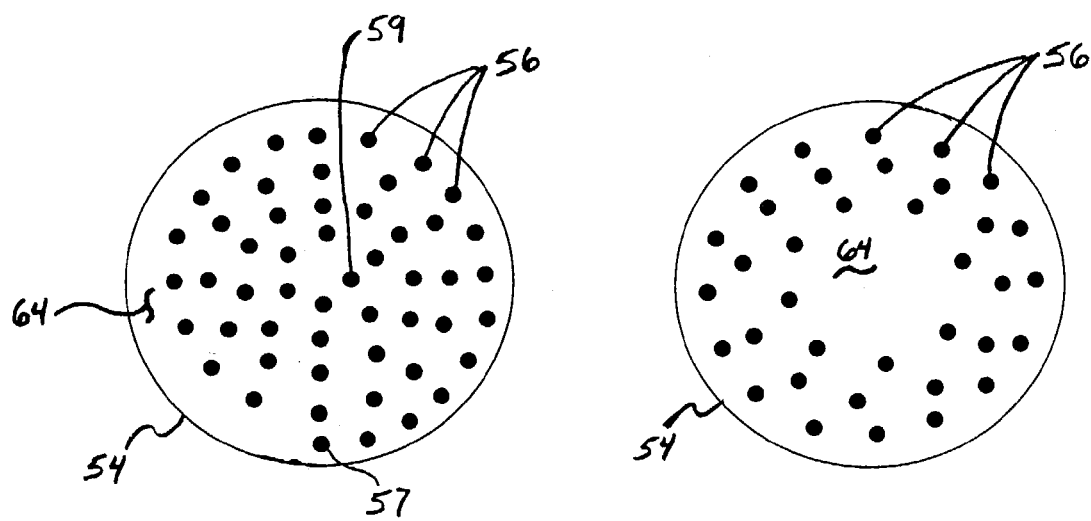
FIGURE 4A        FIGURE 4B

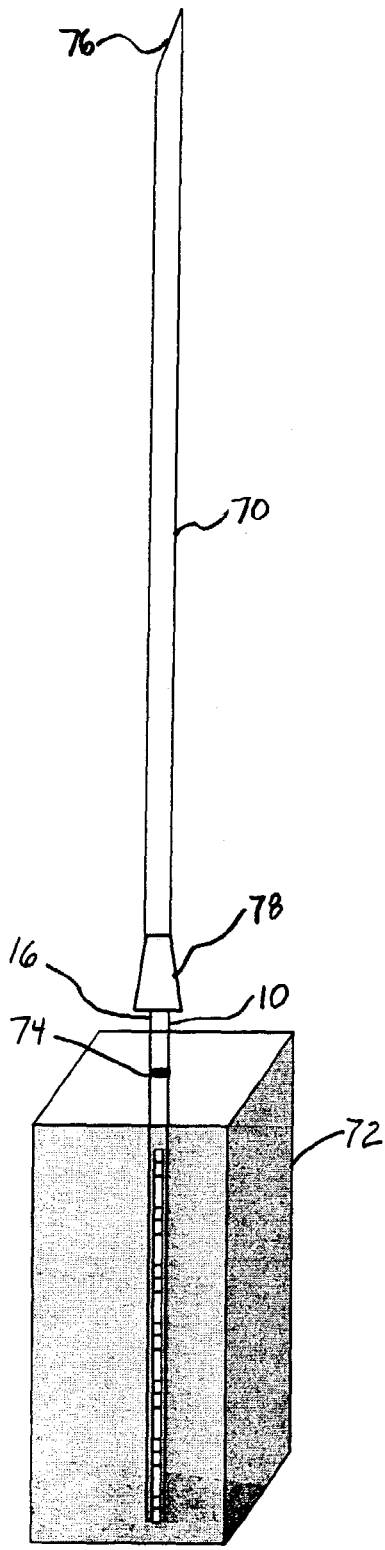 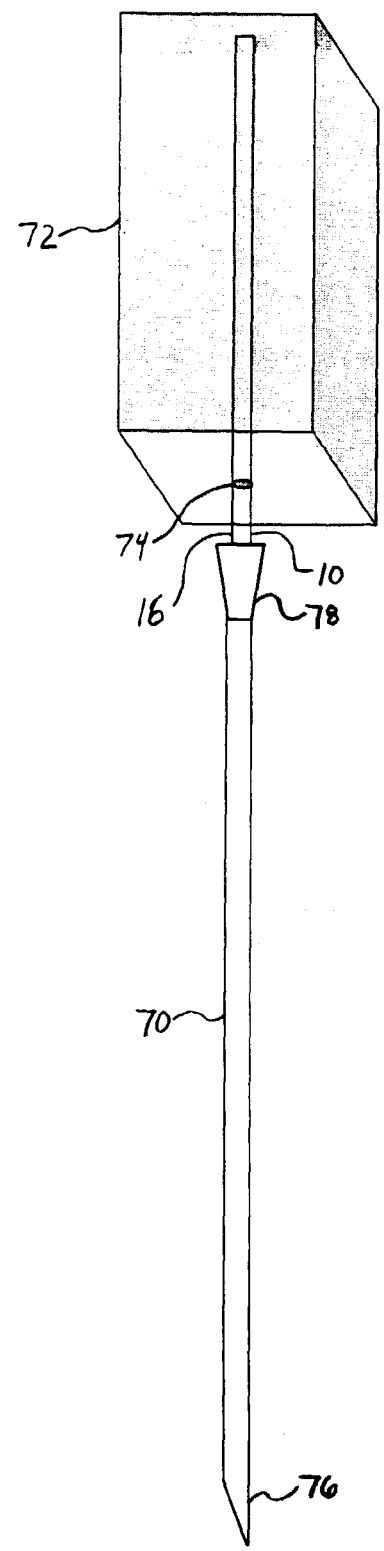
FIGURE 6A FIGURE 6B

BRACHYTHERAPY SEED TRANSPORT DEVICES AND METHODS FOR USING SAME

FIELD OF THE INVENTION

The present invention relates generally to methods and devices for handling and transporting implants. In particular, the invention relates to sleeves that can transport brachytherapy seeds for subsequent use in a variety of implantation needles.

BACKGROUND OF THE INVENTION

Brachytherapy involves the placement of low-dose radiation sources in a pre-determined pattern within a tumor, and has been found to be an accepted alternative to general surgery for the treatment of cancer, particularly for the treatment of prostate cancer. Langely et al. "Prostate brachytherapy has come of age: a review of the technique and results" R. BJU Int'l., 89, 241–249 (2002).

The low-dose sources (known as "radioactive sources", "implants", "brachytherapy seeds", or simply "seeds") typically have an outer shell made of a biocompatible material, such as titanium, that encapsulates a radioactive source (typically 0.1–2.0 mCi of either $^{125}$I or $^{103}$Pd). Commercially available seeds include Symmetra® I-125 (Bebig GmbH, Germany); Iogold™I-125 and Iogold™ Pd-103 (North American Scientific, Inc., Chatsworth, Calif.); Best® I-125 and Best® Pd-103 (Best Industries, Springfield, Va.); Brachyseed® I-125 (Draximage, Inc., Canada); Intersource® Pd-103 (International Brachytherapy, Belgium); Oncoseed®I-125 (Nycomed Amersham, UK); STM 1250 I-125 (Sourcetech Medical, Carol Stream, Ill.); Pharmaseed®I-125 (Syncor, Woodland Hills, Calif.); Prostaseed™ I-125 (Urocor, Oklahoma City, Okla.); I-plant® I-125 (Implant Sciences Corporation, Wakefield, Mass.); Advantage™ I-125 IsoAid Inc. (Port Richey, Fla.); TheraSeed® Pd-103 (Theragenics, Buford, Ga.); Prospera® Pd-103 (North American Scientific, Inc.); and IsoSeed® I-125 (Isotope Products Laboratories (IPL), Valencia, Calif.). The seeds typically are sized to fit down the lumen of a brachytherapy needle. Most such needles are about 18 gauge, and the seeds typically have a diameter of about 0.8 mm and a length of about 4.4 mm.

The seeds preferably are placed within a tumor in a pattern that provides a maximum, cytotoxic dose to the cancerous cells but leaves normal tissue unaffected. Biodegradable, biocompatible spacers can be positioned between the seeds to maintain a desired spacing. Implantation of the seeds and spacers typically is achieved by loading them in a generally linear fashion into a needle and inserting the loaded needle into the tumor. A long stylet is then inserted into the proximal end of the needle and positioned against the terminal seed or spacer. The needle is then removed from the tumor, leaving the seeds and spacers essentially in place.

Brachytherapy seeds are commonly shipped in a non-sterile state in a glass vial. Upon receipt, hospital personnel sterilize the seeds and a radiation physicist loads them, along with spacers, into the lumen of a pre-plugged needle. This is a tedious task involving a significant radiation dose to the physicist performing the loading, and potentially to the hospital personnel in charge of sterilization.

U.S. Pat. No. 6,554,760 discloses one alternative to shipping non-sterile brachytherapy seeds. In particular, the patent discloses an assembly in which the seeds are pre-loaded into a needle and sterilized at the factory. Upon delivery to the hospital, the assembly is then ready for use without need for further sterilization.

U.S. Pat. No. 6,530,875 discloses a brachytherapy seed deployment system in which sterilized seeds and spacers are pre-loaded into a transparent tubular sleeve at the factory. The sleeve is inserted into a needle designed to receive the sleeve, and the needle/sleeve composite structure is used in an implantation procedure.

A need still exists for alternative ways to provide pre-sterilized seeds and spacers in a format that allows for facile loading into a variety of the different types of needles used for brachytherapy, and also allows for ready verification of the loading pattern and activity.

SUMMARY OF THE INVENTION

In one aspect, the present invention provides sleeves for transporting brachytherapy seeds. Preferred sleeves include a first end, a second end, and a substantially transparent lateral wall extending between the ends that defines an interior volume. In preferred embodiments, the lateral wall of the sleeve is made of a substantially non-shielding material. The first end of the sleeve can be sealed in a substantially permanent manner. A plurality of brachytherapy seeds and spacers can be placed in the sleeves in accordance with a patient's treatment plan. The seeds can vary in type and activity within a sleeve in accordance with the patient's treatment plan. The sleeve causes the seeds and spacers to align in a linear manner. After loading, a second seal can be affixed to the lateral wall at the second end. The seeds and spacers can be loaded into a variety of needles by breaching the first or second seal, placing an inverted needle over the sleeve, and inverting the loaded sleeve so that the seeds and spacers are transferred to the needle by gravity.

In certain preferred embodiments, the plurality of brachytherapy seeds include a first seed having a first seed radioactivity level and a second seed having a second seed radioactivity level. The first seed radioactivity level can be less than or greater than the second seed radioactivity level.

In certain preferred embodiments, the substantially transparent lateral wall is made from polyester, polycarbonate, polyimide, glass, polypropylene, polyethylene terephthalate, polyetheretherketone, polyamideimide, and polyetherimide to allow for inspection and verification of the seeds prior to use.

The first and second seals can be substantially permanent or temporary. Permanent seals are breached by cutting the sleeve. Substantially permanent seals include crimping, heat shrink tubing, and curable polymers. Temporary seals can be removed and replaced onto the sleeve.

In certain preferred embodiments the first and second seals form a hermetic seal. In other embodiments, one or both of the first and second seals prevent the passage of seeds and spacers, but allow other fluids and particles to pass through. Non-hermetically sealed sleeves facilitate certain sterilization methods, such as gas sterilization, known to those skilled in the art.

The present invention also provides systems for transporting seeds. The systems includes sleeves and a transfer device. The transfer device includes a first surface at a first end, a second surface at a second end, at least one lateral wall extending between the ends, and multiple apertures that can hold sleeves. The transfer device can be hermetically sealed. In certain preferred embodiments, the transfer device is further packaged in a shipping canister. The canister can be made of lead for shielding. The use of a lead canister allows the entire assembly (sleeves, transfer device, and canister) to be sterilized by using gamma sterilization, for example.

The present invention also provides holders for the sleeves that can be formed from a substantially transparent material. The holders have a first surface at a first end, a second surface at a second end, at least one lateral wall extending between the ends, and at least one aperture in the first surface adapted to receive a sleeve. The holder can be made from a radiation absorbing material that can absorb substantially all radiation emitted by the sleeve.

The present invention also provides methods for transporting brachytherapy seeds. The methods utilize a sleeve that is filled with seeds. Spacers can also be placed in the sleeves. The sleeves can be positioned in a holder and filled manually or with robotic arms. The sleeves are then sealed to prevent the seeds from escaping. In preferred embodiments, the sleeves are placed in a transfer device. In another embodiment, the loaded transfer device can be placed in a canister for shipping.

Other features of the inventions are described below.

BRIEF DESCRIPTION OF THE DRAWINGS

The features and advantages of the present inventions will be more clearly understood from the following drawings that represent non-limiting examples of the inventions. The different figures represent:

FIG. 3 shows a perspective view of an exemplary transfer device;

FIG. 4A shows a top view of a transfer device showing the apertures configured in a spiral pattern;

FIG. 4B shows a top view of a transfer device showing the apertures configured in a concentric pattern;

FIG. 6A shows perspective view of a loaded sleeve in a holder in preparation for needle loading; and FIG. 6B shows a perspective view of a sleeve in an inverted holder during needle loading.

DETAILED DESCRIPTION OF ILLUSTRATIVE EMBODIMENTS

Figure 1:
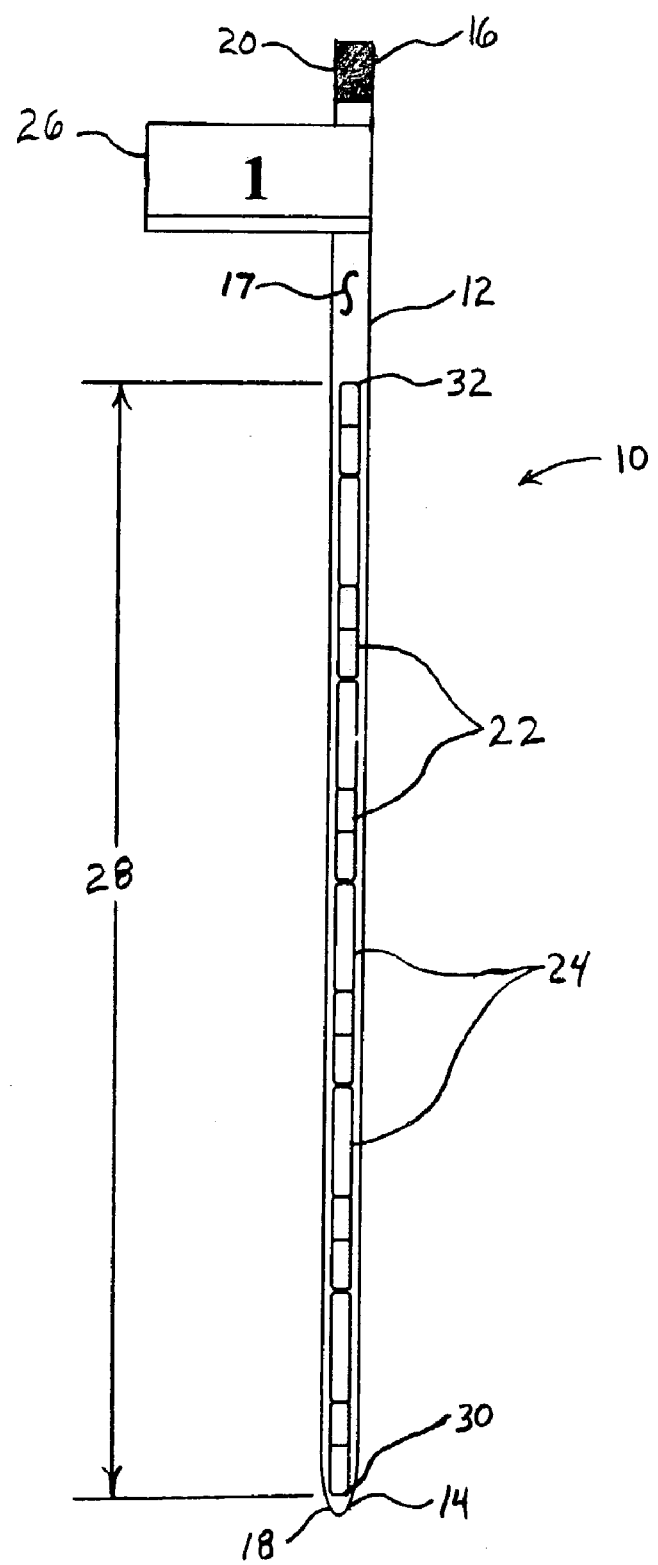
FIG. 1 shows an elevational view of an exemplary sleeve loaded with seeds and spacers.

The present invention generally provides methods of handling and transporting brachytherapy seeds and spacers. In certain preferred embodiments, seeds and spacers are loaded, according to the patient's treatment plan, into a substantially transparent sleeve that has been sealed at one end. Upon loading, the other end of the sleeve is sealed and the sleeve is identified with a label that matches a needle in the patient's treatment plan. The seeds can vary in type and activity within a sleeve in accordance with the patient's treatment plan. In certain preferred embodiments, the sleeves are arranged in a predetermined order in a transfer device that is covered and sealed. Subsequently, the transfer device is placed into a canister, such as a shielded lead pot, and the entire package is sterilized. The package is then shipped to the end user.

Upon receipt, the lid of the canister and cover of the transfer device can be removed to reveal the labeled sleeves. In preferred embodiments, the lower portion of the sleeves remain contained within the canister and transfer device, one or both of which provide radioactivity shielding. Making use of local shielding such as a lead glass or plastic shield, the physicist can transfer a sleeve to a holder according to the invention, and can safely inspect the contents of each sleeve prior to loading the seeds and spacers into a delivery needle.

The radioactivity of each sleeve of seeds can be verified using a dose calibrator or an ionization chamber. In certain embodiments, the dose calibrator or ionization chamber is configured to verify the radioactivity profile of the loading pattern of the seeds within the sleeve. In certain preferred embodiments, the sleeve is made of a thin plastic with little shielding, and the correction that must be applied for attenuation is insignificant. In certain preferred embodiments, the lateral wall of the sleeve is made of a substantially non-shielding material. The term "non-shielding material" refers to a material that allows a majority of radioactivity from a source to pass through. Preferably, the non-shielding material absorbs less than 5% of the radiation emitted by the source. More preferably, the non-shielding material absorbs less than 2% of the radiation emitted by the source. In other embodiments, the non-shielding material absorbs less than 1% or substantially none of the radiation emitted by the source. In certain preferred embodiments, the sleeve is hermetically sealed (i.e., sealed in any manner known in the art that prevents material ingress or egress to an extent that would materially affect the sleeve's functional properties) and can be handled outside of a sterile environment without risk of breaching sterility.

The seeds and spacers can be loaded into a variety of the different types of needles used for brachytherapy. In certain preferred embodiments, this is accomplished by transferring the desired sleeve to a holder, cutting a seal from the sleeve with a cutting tool, placing an appropriately labeled, pre-plugged needle over the end of the sleeve such that the lumen and sleeve meet, and inverting the entire assembly. Since the contents of the sleeve are shielded by the holder, preferably made of lead plastic, and the contents of the needle are typically shielded by stainless steel, there is little exposure to the operator during the transfer.

The sleeves and systems of the present invention can be used in conjunction with existing needle types that are typically filled one seed at a time. Commercially available brachytherapy needles include Isotrack™ Brachytherapy Needle and Set, and Cook® Brachytherapy Needle and Set (Cook Urological, Inc., Spencer, Ind.); Seed Lock2™ and Readi Load™ (World Wide Medical Technologies, Woodbury, Conn.); and RTP Metal Hub Pre-Loaded Needle Sets and RTP Plastic Hub Pre-Loaded Needle Sets (Radiation Therapy Products, Seattle, Wash.).

FIG. 1 shows an exemplary sleeve 10. As shown in FIG. 1, the exemplary sleeve 10 includes a lateral wall 12, a first end 14, a second end 16, a sleeve interior volume 17, and a label 26. Brachytherapy seeds 22 and spacers 24 are disposed in the sleeve interior volume 17. A first seal 18 is located at the first end 14 of the sleeve 10. A second seal 20 can be located at the second end 16 of the sleeve 10.

Lateral wall 12 preferably is made of a rigid material such as polyester, polycarbonate, polyimide, glass, polypropylene, polyethylene terephthalate, polyetheretherketone, polyamideimide, and polyetherimide. Lateral wall 12 can also include other materials, such as metals, so long as the spacer/seed loading pattern can be visually determined. For example, the lateral wall 12 can be made from stainless steel with a polycarbonate window. Preferably, the lateral wall is substantially transparent. In this respect, the term "substantially transparent" is intended to refer to materials and/or combinations of materials that permit a user to visually observe at least a portion of the seeds or spacers contained in the sleeve. Although in preferred embodiments the lateral wall is transparent, it also can be translucent or semi-opaque. In preferred embodiments, the transparent portion of the lateral wall 12 extends so that all of the seeds 22 or spacers 24 contained in the sleeve 10 can be seen through the lateral wall 12 without manipulating the sleeve 10.

In preferred embodiments, the lateral wall 12 has a circular cross-section. Alternatively, the lateral wall 12 can form other cross-sectional shapes, including an oval or square shape, for example. The cross-sectional area should be dimensioned to allow seeds and spacers to slide through the sleeve interior volume without the possibility of passing one another or flipping longitudinally. In preferred embodiments, the cross-sectional area formed by the lateral wall is approximately equal to the cross-sectional area of the lumen of the specified needle to be used.

The term "seal" as used herein refers to a structure that, while intact, will prevent passage of a seed. It may be possible, but is not necessary, that fluids (such as air and water) and particles smaller than the seed will be able to pass through a seal. When referring to a seal that prevents the passage of seeds, fluids, and such particles, the term "hermetic seal" or "hermitically sealed" is used.

In preferred embodiments, the first end 14 of the sleeve 10 is sealed prior to loading. In certain preferred embodiments, the first seal 18 is integrally formed with the lateral wall 12 using techniques know to those skilled in the art. In other embodiments, a cap is used to create a first seal 18. The cap can be press fitted to form a hermetic seal. Alternatively, the cap can be a pliable substance that is formed to fit and seal the first end 14 of the sleeve 10. The pliable substance can be wax, such as bone wax, or it may comprise a curable polymer. In other embodiments, the first seal 18 is formed by crimping the first end 14 of the sleeve 10 using heat and/or pressure. The first seal can also be formed by melting the first end 14 of the sleeve 10 using an organic solvent.

The first seal 18 can be substantially permanent or removable. The term "substantially permanent" refers to seal that cannot be displaced or breached through an application of force of a magnitude employed to deploy seeds from needles during their implantation into a tumor. In certain embodiments, permanent seals cannot be removed without altering or damaging the first end or second end of the lateral wall. A crimp seal is one example of a substantially permanent seal. Substantially permanent seals can be breached by simply cutting the sleeve 10 to remove the first seal 18 or second seal 20. The term "removable" refers to seals that can be displaced using normal manual force, typically without altering or damaging the ends of the lateral wall 12. A threaded cap and wax are examples of a removable seal.

In FIG. 1, the seeds 22 and spacers 24 are aligned linearly to form a deployable load length 28. The load length 28 has a trail end 30 and a lead end 32. The term "lead end" means the end that is closest in proximity to the tip of a needle after loading or the end that enters the body first after deployment from the needle. The term "trail end" means the end opposite the lead end. The lead end precedes the trail end into the patient upon deployment. In preferred embodiments, the trail end is loaded into the sleeve 10 first and the lead end exits the sleeve 10 first during needle loading.

Figure 2:
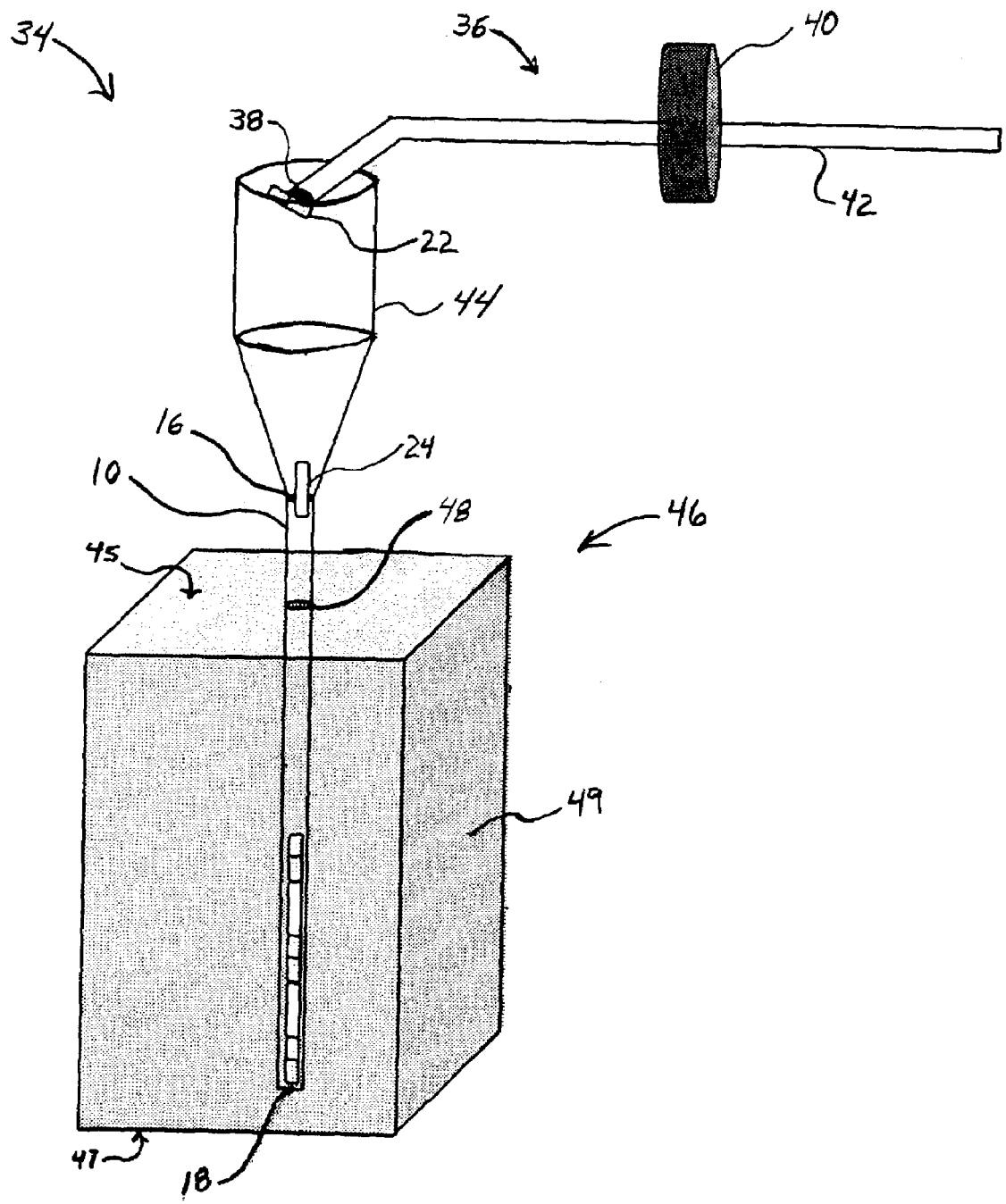
FIG. 2 shows a perspective view of an exemplary sleeve in a loading station.

FIG. 2 shows a sleeve 10 with a first seal 18 being loaded in a loading station 34. As shown in FIG. 2, the loading station includes a loading tool 36, a funnel 44, and a holder 46. The holder 46 has a first surface 45 at a first end, a second surface 47 at a second end, at least one lateral wall 49 extending between the ends, and at least one aperture 48 in the first surface 45 adapted to receive a sleeve.

In certain preferred embodiments, the holder 46 is made of a radiation absorbent material with a bore dimensioned to accept a sleeve. The term "radiation absorbent material" refers to materials that absorb a majority of radioactivity emitted from the seeds. Preferably, the radiation absorbent material absorbs at least 90% of the radiation emitted by the sleeve. More preferably, the radiation absorbent material absorbs at least 99% of the radiation emitted by the sleeve. In other embodiments, the radiation absorbent material absorbs at least 99.9% or substantially all of the radiation emitted by the sleeve.

In preferred embodiments, the holder is substantially transparent so that an operator can visualize the seeds and spacers during the loading operation. In certain preferred embodiments, the holder 46 is made from lead plastic. The holder can also be made from lead glass. The holder can include multiple bores for holding multiples sleeves.

As shown in FIG. 2, a funnel 44 can be positioned proximate the second end 16 of the empty sleeve 10. The seeds 22 and spacers 24 can be dropped into the funnel 44 and loaded into the sleeve 10 according to the treatment plan. This task can be accomplished manually using the exemplary loading tool 36 shown in FIG. 2. The loading tool 36 consists of a tube 42 attached to a vacuum line. In preferred embodiments, the tube 42 is made of stainless steel. Attached to the loading tool 36 is a shield 40 that is made of aluminum or a similar lightweight material that will provide some shielding to the person loading the sleeve 10. The task of loading sleeves can also be done using robotic equipment known to those skilled in the art. In other embodiments, a loading tool uses a mechanical grip to move the seeds and spacers.

A patient may benefit from a loading pattern of seeds in the sleeve that includes seeds that vary in type and/or radioactivity. The term "loading pattern" refers to the sequence of seeds or seeds and spacers within a sleeve. For example, the loading pattern can include seeds with relatively higher levels of radioactivity near the lead end, and seeds with relatively lower levels of radioactivity near the trail end. Alternatively, the patient's treatment plan may benefit from higher levels of radiation near the center or trail end of the deployable load length. Different types of spacers can also be used to create a loading pattern configured to meet a patient's treatment plan. The spacers can vary in length, for example, so that seeds in one portion of the deployable load length can be positioned closer or farther away from one another as compared to seeds in another portion of the deployable load length.

After loading, the second end 16 of the sleeve 10 can be sealed. In certain preferred embodiments, the second seal 20 is a cap or press-fitted plug made of metal, plastic, or wax, for example. The cap can be press fitted to form a hermetic seal. Alternatively, the cap can be a pliable substance that is formed to fit and seal the second end 16 of the sleeve 10. The pliable substance can be wax, such as bone wax, or it may comprise a curable polymer, such as epoxy, for example. In other embodiments, the second seal 20 is formed by crimping the second end 16 of the sleeve 16 using heat and/or pressure. The second seal 20 can be permanent or removable.

In another embodiment, the second seal 20 is not hermetically sealed. Rather, shrink-wrap tubing is fixed onto the second end 16 of the sleeve 10 and the entire assembly is heated. The shrink-wrap tubing can also be used for the first seal 18. The shrink-wrap tubing shrinks, thus preventing the seeds 22 and spacers 24 from falling out of the ends of the sleeve, while maintaining an opening for sterilants, such as steam, ethylene oxide, or ozone. In certain preferred embodiments, the first seal 18 and second seal 20 of the sleeve 10 are made using a crimp seal.

FIG. 3 shows a transfer device 54 for transporting multiple sleeves 10. As shown in FIG. 3, a cover 52 can be placed on the transfer device 54. The transfer device includes a first surface 64 at a first end, a second surface 66 at a second end, at least one side wall 68 extending between the ends, and a plurality of apertures 56 for placement of multiple sleeves 10. The embodiment shown in FIG. 3 has a cylindrical shape. The transfer device 54 can also be made in other shapes, including a square, oval, rectangle, for example. In certain preferred embodiments, the transfer device 54 is made of plastic. The transfer device 54 can also be made of metal, such as stainless steel or lead, for example. In certain embodiments, the transfer device 54 contains a radiation absorbing material such as a lead salt.

FIG. 4A shows a spiral arrangement of apertures 56 in transfer device 54. The spiral arrangement allows the user to more easily access and identify the sleeves in a sequential manner. For example, the sleeves can be arranged such that the sleeve to be used first is on the outer most hole 57. The last sleeve to be used will be in the inner most hole 59.

FIG. 4B shows a concentric circle arrangement of apertures 56 in transfer device 54. Like the spiral arrangement, the concentric circle arrangement allows the user to more easily access and identify the sleeves. The concentric pattern is useful when multiple sleeve types are supplied in a single transfer device. Each concentric circle can be used for a specific sleeve type. Other aperture arrangements can also be used. For example, a square transfer device can be configured with apertures aligned in rows and columns.

Figure 5:
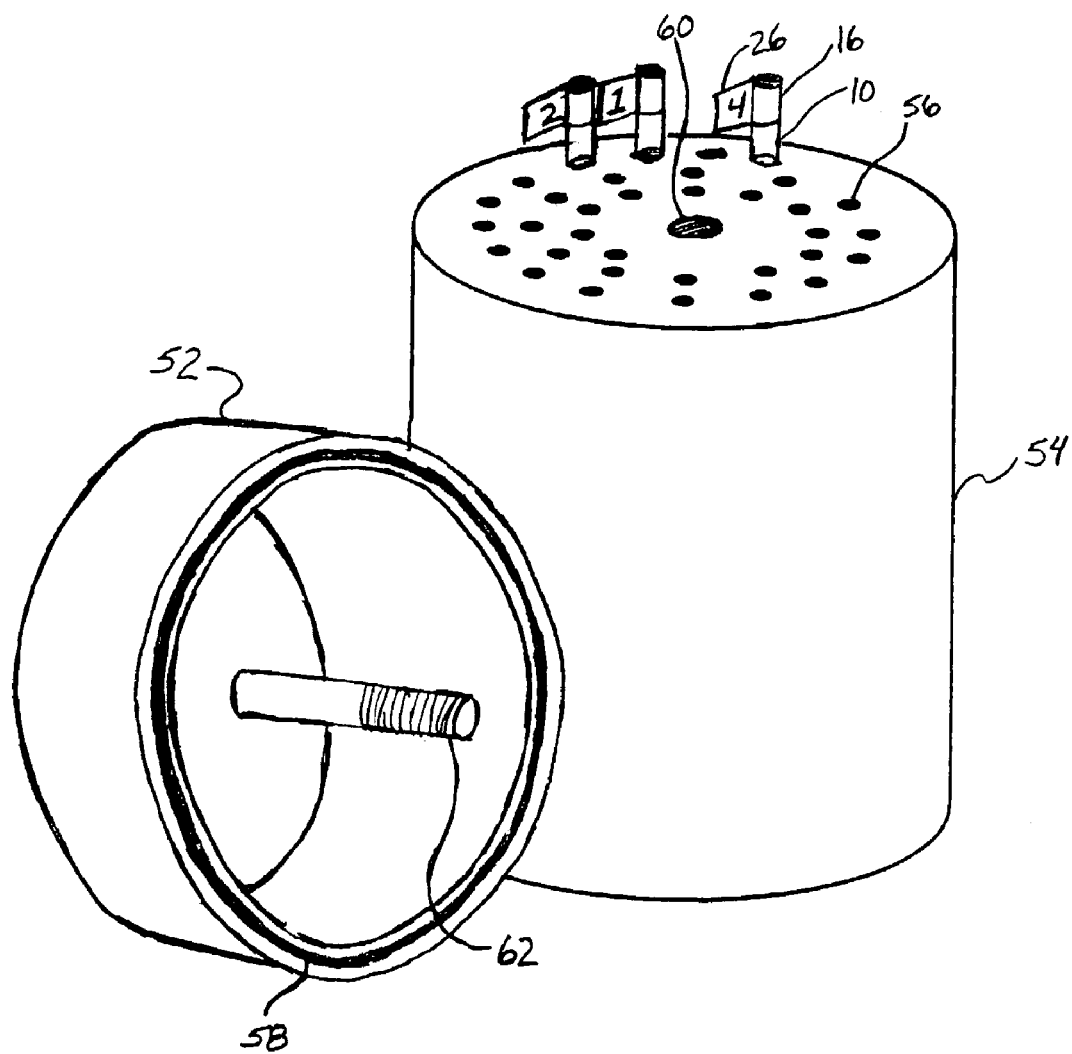
FIG. 5 shows a perspective view of an exemplary transfer device containing three sleeves.

After loading the specified number of sleeves 10 in the apertures 56 in the transfer device 54, the cover 52 is fit onto the transfer device 54. FIG. 5 shows an exemplary transfer device 54 filled with three sleeves and cover 52. As shown in FIG. 5, a seal 58 is used to hermetically seal the transfer device 54. The seal 58 can be an o-ring, as shown in FIG. 5, or other seals known to those skilled in the art. The transfer device 54 can also be hermetically protected by wrapping the transfer device 54 and cover 52 with a film or placing the transfer device 54 and cover 52 in a hermetically sealed bag.

Also shown in FIG. 5 is a threaded socket 60 and threaded pin 62. The cover 52 can be screwed onto the transfer device 54 using the threaded pin 62 and threaded socket 60 to seal the transfer device 54. Other closure mechanisms known to those skilled in the art can be used, including a hinge with clasp, multiple clasps, and tape, for example.

In certain preferred embodiments, the transfer device 54 is placed in a shipping canister (not shown). The canister can include a lid to facilitate placement and removal of the transfer device from within the canister. The canister is preferably made of lead or other radiation absorbing materials. The canister can be exposed to radiation, such as gamma rays, that will sterilize the entire contents. In certain preferred embodiments, the canister is hermetically sealed (in addition to the hermetic sealing of the transfer device 54) for additional protection.

The canister is preferably configured so that only the lid of the canister needs to be removed to remove the transfer device cover 52 and sleeves 10. In certain preferred embodiments, each sleeve 10 is mostly shielded by the transfer device 54 and canister when the canister lid and transfer device cover 52 are removed.

Upon sterilization, the canister is shipped to the end user, who will remove both the lid to the canister and cover 52 of the transfer device 54, exposing the labeled sleeves 10. Using a pair of tweezers or similar tool, the sleeves 10 can be individually removed from the transfer device 54. The activity can be verified using an ionization chamber (or other appropriate equipment) and each sleeve placed into a holder. The loading pattern may then be visually verified with minimal exposure because the holder is preferably made from a substantially transparent radiation absorbing material, such as lead plastic. The loading pattern of the sleeve can also be evaluated by analyzing the radioactivity profile of the sleeve. In certain embodiments, a dose calibrator or ionization chamber is configured to verify the radioactivity profile caused by the loading pattern of the seeds within the sleeve.

FIG. 6A shows a needle 70 in preparation for loading and FIG. 6B shows a needle 70 after loading. As shown in FIG. 6A, a loaded sleeve 10 is placed in holder 72. The sleeve 10 is then opened, using a pair of tweezers or similar tool in the case of a capped or temporarily sealed sleeve, or by using a cutting tool in the case of a permanently sealed sleeve. A pre-plugged needle 70 having a substantially tapered end 76 and a substantially blunt end 78 is positioned so that the substantially blunt end 78 is proximate the second end 16 of the sleeve 10. The entire assembly is then inverted such that the seeds and spacers fall into the needle 70, as shown in FIG. 6B. The seeds are now ready to be implanted into the patient.

It is to be understood that even in the numerous characteristics and advantages of the present invention set forth in the foregoing description and examples, together with details of the structure and function of the invention, the disclosure is illustrative only, and changes can be made to detail, especially in matters of shape, size and arrangement of parts within the principles of the inventions to the full extent indicated by the broad general meaning of the terms in which the appended claims are expressed. For instance, electron beam sterilization, gas sterilization, autoclaving, or similar techniques can be used in addition to gamma sterilization.

What is claimed:

1. A system comprising:
    a transfer device comprising a first surface at a first end, a second surface at a second end, at least one lateral wall extending between said ends, and a plurality of apertures in said first surface; and
    a plurality of sleeves each comprising a first end, a second end, a substantially transparent lateral wall extending between said ends, and a first seal affixed to said lateral wall at said first end, wherein a plurality of brachytherapy seeds are disposed within each of said sleeves and said sleeves are positioned within said apertures.

2. The system of claim 1 wherein said first seal is affixed to said lateral wall in a substantially permanent manner.

3. The system of claim 1 further comprising a second seal affixed to said lateral wall at said second end.

4. The system of claim 1 wherein said brachytherapy seeds are hermetically sealed in said sleeve.

5. The system of claim 1 wherein said plurality of brachytherapy seeds comprise a first seed having a first seed radioactivity level and a second seed having a second seed radioactivity level, wherein said first seed radioactivity level is less than said second seed radioactivity level.

6. The sleeve of claim 1 wherein said lateral wall comprises a substantially non-shielding material.

7. The system of claim 1 further comprising a holder formed from a substantially transparent material, comprising a first surface at a first end, a second surface at a second end, at least one lateral wall extending between said ends, and at least one aperture in said first surface adapted to receive said sleeve.

8. A method comprising the steps of:
providing a sleeve having a first end, a second end, a substantially transparent lateral wall extending between said ends to define a sleeve interior volume, and a plurality of brachytherapy seeds positioned within said sleeve interior volume;
providing a brachytherapy needle having a substantially tapered end, a substantially blunt end, and a lateral wall extending between said ends to define a needle interior volume;
positioning an end of said sleeve proximate said substantially blunt end of said needle;
transferring at least one of said seeds from said sleeve interior volume to said needle interior volume, and
breaching a seal affixed to said lateral wall at one of said ends prior to performing said transferring step.

9. The method of claim 8 wherein a plurality of spacers are positioned between said brachytherapy seeds, and said seeds and said spacers are positioned in said sleeve in a predetermined sequence.

10. A method comprising the steps of:
providing a sleeve that comprises a first end, a second end, a substantially transparent lateral wall extending between said ends, and a first seal affixed to said lateral wall in a substantially permanent manner at said first end; and
placing a plurality of brachytherapy seeds in said sleeve through said second end;
providing a transfer device comprising a first surface at a first end, a second surface at a second end, at least one lateral wall extending between said ends, and a plurality of apertures in said first surface adapted to receive said sleeve; and
placing said sleeve in one of said apertures.

11. The method of claim 10 further comprising the step of sealing said second end.

12. The method of claim 10 further comprising the step of placing spacers in said sleeve between said brachytherapy seeds.

13. The method of claim 12 wherein said seeds and said spacers are positioned in said sleeve in a predetermined sequence.

14. The method of claim 10 further comprising the step of sterilizing said transfer device containing said sleeve.

15. The method of claim 10 further comprising the step of placing a cover over said sleeve and said first end of said transfer device.

16. A method comprising the steps of:
providing a transfer device comprising:
a first surface at a first end,
a second surface at a second end,
at least one lateral wall extending between said ends,
at least one sleeve comprising a first end, a second end, a substantially transparent lateral wall extending between said ends to define a sleeve interior volume, and a plurality of brachytherapy seeds positioned within said sleeve interior volume; and
a plurality of apertures in said first surface adapted to receive said sleeve;
removing said sleeve from said transfer device; and
removing at least one of said seeds from said sleeve interior volume.

17. The method of claim 16 further comprising the steps of:
providing a brachytherapy needle having a substantially tapered end, a substantially blunt end, and a lateral wall extending between said ends to define a needle interior volume;
positioning an end of said sleeve proximate said substantially blunt end of said needle;
transferring at least one of said seeds to said needle interior volume.

18. The method of claim 16 wherein said sleeve comprises a seal affixed to said lateral wall at one of said ends.

19. The method of claim 16 further comprising the step of breaching said seal.

20. The method of claim 19 wherein said seal is breached by cutting said sleeve to remove said seal.

21. A device formed from a substantially transparent material, comprising a first surface at a first end, a second surface at a second end, at least one lateral wall extending between said ends, at least one aperture in said first surface, and a sleeve within said aperture comprising a first end, a second end, a substantially transparent lateral wall extending between said ends, and a plurality of brachytherapy seeds disposed within said sleeve.

22. The device of claim 21 wherein said material absorbs substantially all radiation emitted by said seeds.

23. The device of claim 22 wherein said material comprises at least one lead salt.

24. A device of claim 21 wherein said plurality of brachytherapy seeds comprise a first seed having a first seed radioactivity level and a second seed having a second seed radioactivity level, wherein said first seed radioactivity level is less than said second seed radioactivity level.

25. A device formed from a substantially transparent material, comprising a first surface at a first end, a second surface at a second end, at least one lateral wall extending between said ends, and at least one aperture in said first surface including a removable sleeve comprising a first end, a second end, a substantially transparent lateral wall extending between said ends, and a plurality of brachytherapy seeds disposed within said sleeve.

* * * * *